(12) United States Patent
Koch

(10) Patent No.: US 6,578,573 B2
(45) Date of Patent: Jun. 17, 2003

(54) DEVICE FOR RELEASING A GAS TO A RESPIRATOR

(75) Inventor: Jochim Koch, Ratzeburg (DE)

(73) Assignee: Drager Medical AG & Co. KGAA (DE)

( * ) Notice: Subject to any disclaimer, the term of this patent is extended or adjusted under 35 U.S.C. 154(b) by 0 days.

(21) Appl. No.: 10/025,141

(22) Filed: Dec. 19, 2001

(65) Prior Publication Data

US 2002/0050275 A1 May 2, 2002

(30) Foreign Application Priority Data

Feb. 28, 2000 (DE) .......................... 101 09 671

(51) Int. Cl.[7] .................................. A62B 9/04
(52) U.S. Cl. ........................ 128/202.27; 128/200.14; 128/200.23; 128/202.27; 128/205.21; 239/337; 222/325; 222/402.1; 222/402.13; 222/402.14; 222/153.09; 222/153.1; 604/110
(58) Field of Search ................. 128/200.14, 200.23, 128/202.27, 205.21; 289/337; 222/325, 402.1, 402.13, 402.14, 153.09, 153.1; 604/110

(56) References Cited

U.S. PATENT DOCUMENTS

| | | | | |
|---|---|---|---|---|
| 3,935,974 A | * | 2/1976 | Weyn .................. | 222/402.13 |
| 3,946,911 A | * | 3/1976 | Morane et al. ........ | 222/402.11 |
| 4,577,803 A | * | 3/1986 | Owen .................. | 239/690 |
| 4,962,868 A | * | 10/1990 | Borchard .............. | 222/49 |
| 5,031,800 A | * | 7/1991 | Brunet ................ | 222/153.06 |
| 5,293,865 A | * | 3/1994 | Altner et al. ......... | 128/203.12 |
| 5,431,155 A | * | 7/1995 | Marelli ............... | 128/200.14 |
| 5,456,668 A | * | 10/1995 | Ogle, II .............. | 604/110 |
| 5,474,758 A | * | 12/1995 | Kwon ................. | 424/45 |
| 5,476,106 A | * | 12/1995 | Gartz ................. | 128/898 |
| 5,682,875 A | * | 11/1997 | Blower et al. ......... | 128/200.23 |
| 6,113,008 A | * | 9/2000 | Arsenault et al. ...... | 239/337 |
| 6,460,537 B1 | * | 10/2002 | Bryant et al. ......... | 128/200.23 |

* cited by examiner

Primary Examiner—Glenn K. Dawson
Assistant Examiner—Michael Mendoza
(74) Attorney, Agent, or Firm—McGlew and Tuttle, P.C.

(57) ABSTRACT

A device for releasing a gas to a respirator with a compressed gas cylinder (2), which contains the gas and has a metering valve (6). The metering valve (6) can be opened by pressure. The metering valve (6) has a tubular valve body (7) letting through the gas and has a collar (5) surrounding the valve body (7). A cylinder adapter has a locking mechanism (16) designed for fastening to the collar (5). The cylinder adapter (1) always remains associated with the corresponding compressed gas cylinder (2). This is accomplished by a predetermined breaking point with reduced strength properties being provided on the cylinder adapter (1). The breaking point is intended to destroy the locking mechanism (16) during the removal of the cylinder adapter (1) from the collar (5).

22 Claims, 3 Drawing Sheets

US 6,578,573 B2

DEVICE FOR RELEASING A GAS TO A RESPIRATOR

FIELD OF THE INVENTION

The invention relates generally to respirators and more particularly to respirators that also assume a measurement task such as the determination of the functional residual capacity of the lungs

BACKGROUND OF THE INVENTION

Respirators are usually operated with a mixture of oxygen and air. Laughing gas is also added as another gas in inhalation anesthesia apparatus. These gases are made available from a central gas supply unit in medical treatment rooms by plug type couplings. These supply the respirator with the necessary gas in the treatment rooms. Besides the pure respiration, respirators nowadays also increasingly assume measurement tasks, e.g., the determination of the functional residual capacity of the lungs during artificial respiration. A test gas is mixed with the breathing gas for this purpose, and this test gas is supplied newly for each breath. With the knowledge of the patient-specific residual capacity, the respiration parameters can be better adapted to the patient. As a consequence of this, the respiration can be carried out in a gentler manner. A respirator for determining the functional capacity has become known from EP 791 327 A2.

The test gas is fed in usually from commercially available compressed gas cylinders. The cylinders must be fastened on a separate cylinder cart because of their size. Such a cylinder usually used has, e.g., a volume of 10 L. This makes handling of such cylinders difficult in routine clinical operations. The measurement tasks must be performed only at certain points in time within set time periods. The cylinder cart with the compressed gas cylinder is not needed during the rest of the time. If measurement tasks are performed on different patients, the cylinder cart must be transported to another patient bed. Only comparatively small volumes of the test gas are needed for the measures that usually need to be performed, so that it is not necessary to keep ready an excessively large gas reserve at the respirator.

Besides helium as the test gas, heptafluoropropane is also suitable; in addition, this has the advantage of being able to be stored in the liquid form. Heptafluoropropane has, e.g., a vapor pressure of 3.9 bar absolute at a room temperature of 20° C. and a vapor pressure of 7 bar absolute at 40° C. Due to the liquid storage, a large gas volume can be accommodated in a comparatively small compressed gas cylinder.

SUMMARY AND OBJECTS OF THE INVENTION

A basic object of the present invention is to provide a storage medium with an adapter to provide an additionally needed gas for a respirator in a simple manner and to provide a process for storing a gas for a respirator.

According to the invention, a device is provided for releasing a gas to a respirator. The device includes a compressed gas cylinder which contains the gas. A metering valve is provided that can be opened by pressure. The metering valve includes a valve body (e.g., tubular) letting through the gas and with a collar surrounding the valve body. A cylinder adapter (1, 100) is provided that has a locking mechanism for fastening on the collar and a cylindrical wall part in the area of the valve body. A pressure body can be connected to the wall part via a connection element in such a way that a stroke movement is possible. The pressure body has a pressure piston for actuating the valve body and a gas channel for drawing off the gas to the respirator. A predetermined breaking point with reduced strength properties on the cylinder adapter is employed to destroy or functionally negate the locking mechanism during the removal of the cylinder adapter from the collar.

According to another aspect of the invention, a process is provided for storing a gas for a respirator. A compressed gas cylinder is used as the storage medium for the gas. A metering valve that can be opened by pressure is provided with a tubular valve body and with a collar surrounding the valve body. A cylinder adapter is provided with a locking mechanism such that the locking mechanism can be fastened to the collar. A predetermined breaking point with reduced strength properties is provided on the cylinder holder. The locking mechanism is destroyed during the removal of the cylinder adapter from the collar.

An advantage of the present invention is essentially that due to the combination of a cylinder adapter with a commercially available compressed gas cylinder, as is used, e.g., in spray cans, an inexpensive gas reservoir is made available, which can be connected to the respirator in a simple manner. The cylinder adapter needed for the adaptation is fastened to a collar located in the area of the valve element of the compressed gas cylinder by means of a locking mechanism. In commercially available spray cans, a protective cap, which protects the valve element from damage or accidental operation, is normally located on this collar. The cylinder adapter is provided according to the present invention with a predetermined breaking point, which has a reduced resistance cross section and is intended to destroy the locking mechanism during the removal of the cylinder adapter from the collar. It shall be achieved by means of the predetermined breaking point that the cylinder adapter cannot be fastened to another compressed gas cylinder after removal from the compressed gas cylinder and an undesired gas cannot be fed to the respirator as a result. The cylinder adapter is normally fastened to the collar of the compressed gas cylinder prior to the filling of the compressed gas cylinder. It can be achieved by means of the cylinder adapter that only a certain counterpiece, a pressure body, can be connected to the cylinder adapter in order to remove gas for supply to the respirator. The metering valve of the compressed gas cylinder is opened by pressing the tubular valve body. The pressure body is displaceable for this purpose in relation to a cylindrical wall part on the cylinder adapter in the form of a stroke movement and it has a push rod, which actuates the valve body. Depending on the positioning of the push rod in relation to the valve body, gas can be removed from the compressed gas cylinder. The compressed gas containers used according to the present invention are especially inexpensive because they are manufactured in large lots for different applications.

The connection element is advantageously designed as a bayonet catch, with which the stroke movement can be carried out in a simple manner.

It is especially advantageous to provide the bayonet catch with a park position, which is used to ensure that the pressure body is nevertheless connected to the cylinder adapter with the metering valve closed. The grooves of the bayonet catch are provided for this purpose with depressions used as a locked position for the park position in the areas in which the pin-shaped counterpiece is introduced.

In the area of the collar, the locking mechanism advantageously comprises a support on the cylinder adapter and a counterpiece, which is located at a support ring that is arranged in an annular space between the compressed gas cylinder and a grip shell on the cylinder holder. The grip shell extends, beginning from the collar of the compressed gas cylinder, over a partial area of the outer wall of the compressed gas cylinder.

The predetermined breaking point is arranged according to the present invention in the form of a circular notch in the connection area between the cylindrical wall part, at which the pressure body is located, and the grip shell. The cross section of the wall is reduced by the notch in this area of the cylinder adapter, so that the locking mechanism is destroyed in the area of the predetermined breaking point when the cylinder adapter is pulled off from the collar.

It is particularly advantageous to manufacture the cylinder adapter from two symmetrical housing shells and to be connected to one another via a sealing band. The sealing band is dimensioned such in terms of its strength properties that it will be torn up when the cylinder adapter is pulled off from the collar of the compressed gas cylinder.

According to an advantageous process for storing a gas for a respirator, a compressed gas cylinder is used as the storage medium for the gas, which has a metering valve that can be opened by pressure with a tubular valve body and with a collar surrounding the valve body. A locking mechanism located on a cylinder adapter is designed such that the locking mechanism can be fastened to the collar, and a predetermined breaking point is provided on the cylinder adapter such that it breaks when the cylinder adapter is removed and thus destroys the locking mechanism. It shall be achieved as a result that the cylinder adapter cannot be subsequently mounted on another compressed gas cylinder.

An exemplary embodiment of the present invention is shown in the figure and will be explained in greater detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
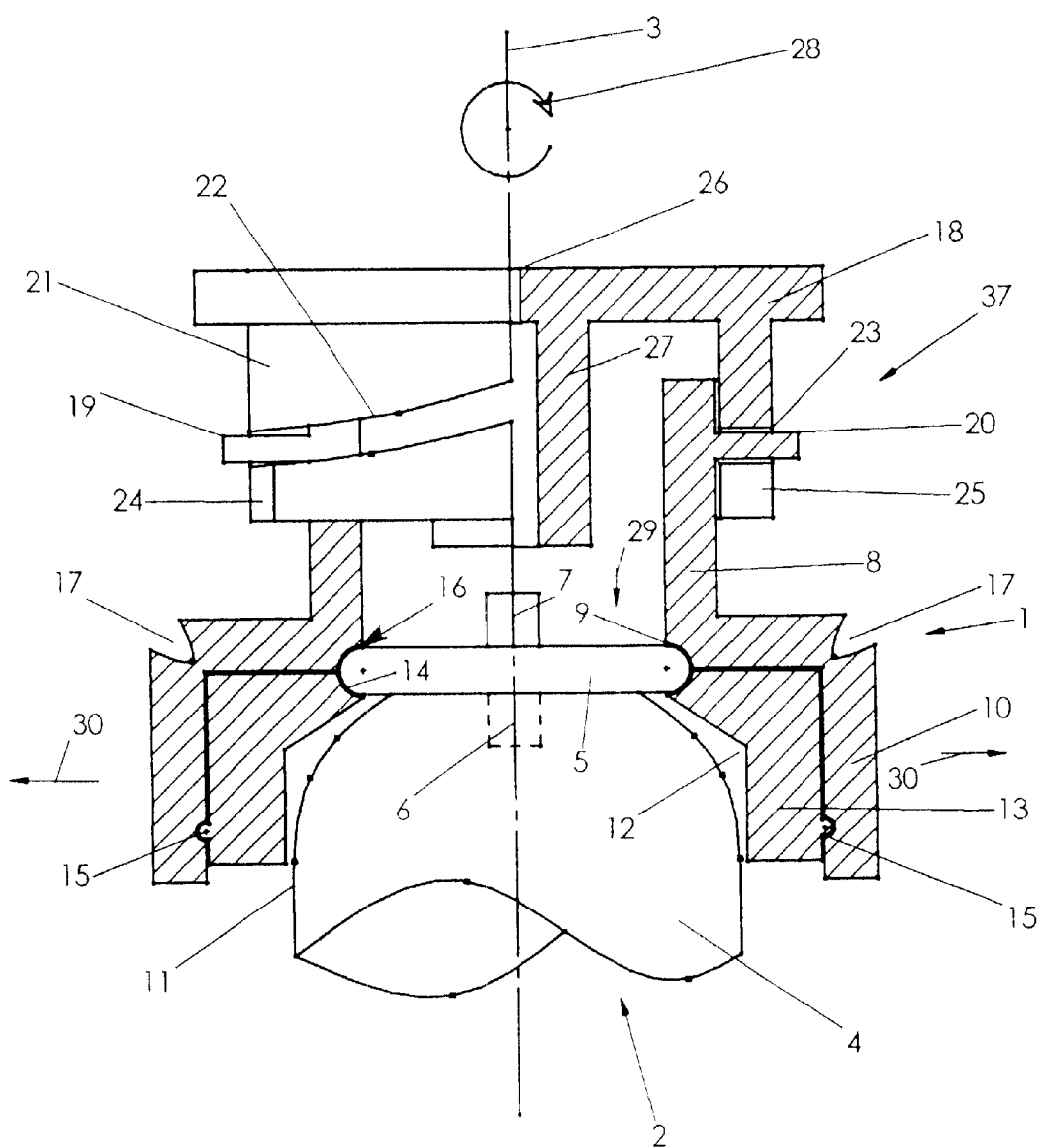
FIG. 1 is a longitudinal sectional view of a cylinder adapter on a compressed gas cylinder with the pressure body attached.

Referring to the drawings in particular, FIG. 1 shows a longitudinal section of a cylinder adapter 1 on a compressed gas cylinder 2 with a pressure body 18, which is shown as a longitudinal section in the area to the right of a central axis 3. The compressed gas cylinder 2 comprises a container 4, which is filled with the gas to be metered. A flanged collar is provided on a top side. On the collar a metering valve 6 with a tubular valve body 7 is mounted. The cylinder adapter 1 is designed in the area of the valve body 7 as a cylindrical wall part in the form of a sleeve 8. A quadrant-like first groove 9 is arranged on the top side of the collar 5. The first groove 9 is located at the lower end of the sleeve 8. The sleeve 8 expands beneath the first groove 9 to a grip shell 10. The grip shell 10 extends approximately in parallel to the outer wall 11 of the container 4. A support ring 13 is in turn in contact with the underside of the collars by means of a quadrant-like second groove 14. The support ring 13 snaps into the grip shell 10 by means of a nose 15 and is pushed in, in an annular space 12 between the grip shell 10, the cylinder adapter 1 and the outer wall 11 of the compressed gas cylinder 2. The first groove 9 and the second groove 14 together form a locking mechanism 16 for the cylinder adapter 1 attached to the collar 5. A circular notch 17 acts as a predetermined breaking point of the cylinder adapter 1. The notch 17 is located in the transition area of the cylinder adapter 1 between the sleeve 8 and the grip shell 10. Two pins 19, 20 pointing vertically to the outside are arranged an the top side of the sleeve 8 for fastening the pressure body 18 on the cylinder adapter 1. The wall part in the form of sleeve 8 may have a gas type specific coding.

The pressure body 18 has a pot-shaped design and is displaceable along the outside of the sleeve 8 in the form of a stroke movement. Helically extending grooves 22, 23, which have openings 24, 25 on the underside of the pressure body 18 for introducing the pins 19, 20, are provided for this purpose in the wall area 21 of the pressure body 18. Together with the grooves 22, 23, the pins 19, 20 form a bayonet catch 37, with which the pressure body 18 and the cylinder adapter 1 are connected. A pressure piston 27, which is provided with a gas channel 26 and via which the gas present in the compressed gas cylinder 2 is removed, is arranged in the middle of the pressure body 18.

The device according to the present invention operates as follows:

After filling the compressed gas cylinder 2, the cylinder adapter 1 is placed on the collar 5 of the compressed gas cylinder 2, and the support ring 13 is pushed into the annular space 12 between the cylinder adapter 1 and the compressed gas cylinder 2 until the second groove 14 lies on the underside of the collar 5. The noses 15 now snap into the cylinder adapter 1. The support ring 13 is thus nondetachably connected to the cylinder adapter 1. The pressure body 18 is connected to a respirator, not shown in FIG. 1. If an additional gas is needed to be fed to the respirator, the pressure body 18 with its openings 24, 25 is attached to the pins 19, 20 of the cylinder adapter 1 and then rotated in the direction of arrow 28. Due to the helical arrangement of the grooves 22, 23, the pressure body 18 is pressed with the pressure piston 27 in the direction of the arrow 29 against the valve body 7 and the metering valve 6 opens. The gas present in the compressed gas cylinder 2 can now flow off via the gas channel 26. If the cylinder adapter 1 is removed from the collar 5, the grip shells 10 undergo a deformation in the direction of arrow 30, because the support ring 13 is pushed from the underside of the collar 5 to the top side of the collar. The material thickness of the cylinder adapter 1 in the area of the notch 17 is selected to be such that the grip shells 10 break off in the area of the notch 17 from the cylinder adapter 1 during the removal of the cylinder adapter 1 from the compressed gas cylinder 2 and thus the cylinder adapter 1 cannot be used again.

Figure 2:
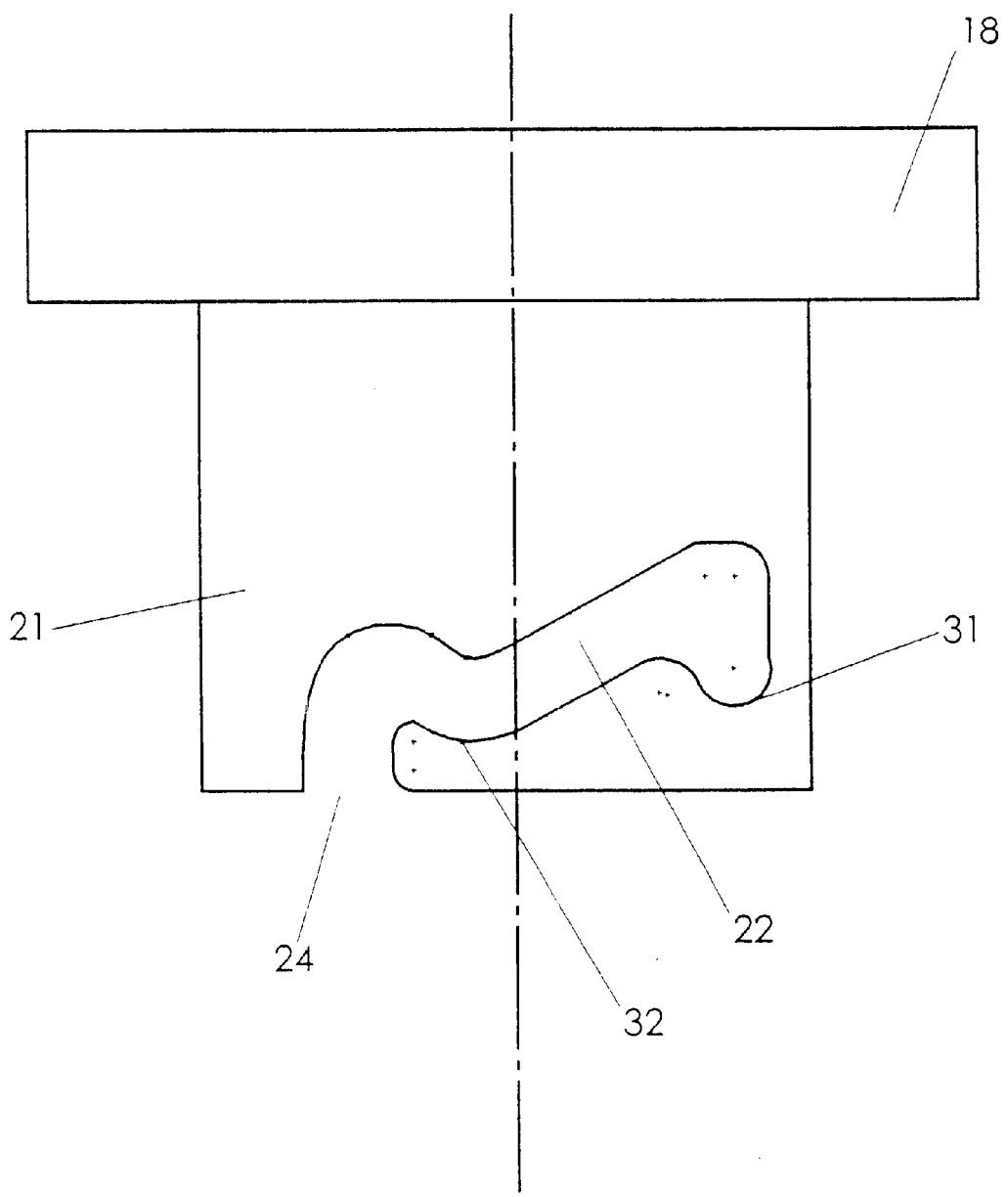
FIG. 2 is a side view of the pressure body.

FIG. 2 illustrates a side view of the pressure body 18 with the helical groove 22 and the opening 24. The other helical groove 23, FIG. 1, is located on the opposite side and is not shown in FIG. 2. In the coupled state, the pin 19, FIG. 1, is in a first depression 31, so that the pressure body 18 is locked against the cylinder adapter 1. A second depression 32 in the area of the opening 24 acts as a park position, in which the pressure body 18 is mechanically connected to the cylinder adapter 1, but the metering valve 6, FIG. 1, is not yet opened.

Figure 3:
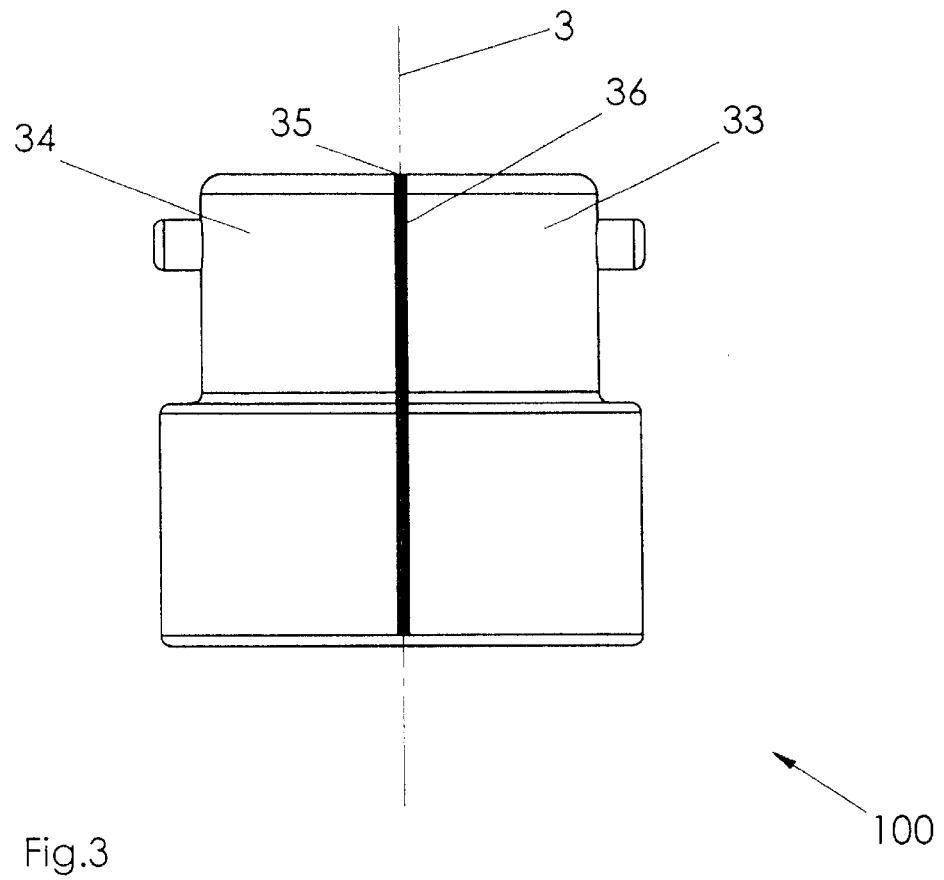
FIG. 3 is a view of an alternative embodiment of a cylinder adapter.

FIG. 3 illustrates an alternative embodiment of a cylinder adapter 100, which comprises two housing shells 33, 34, which are connected to one another at a partition line 35 via a sealing band 36. The strength of the sealing band 36 is selected to be such that it breaks when the cylinder adapter 100 is pulled off from the collar 5 of the compressed gas cylinder 2, FIG. 1, and the cylinder adapter 100 thus falls apart into its housing halves 33, 34. The sealing band is the predetermined breaking point of the cylinder adapter 100. The locking mechanism between the cylinder adapter 100 and the compressed gas cylinder 2 is not shown in greater detail in FIG. 3 because it corresponds to that shown in FIG. 1.

Figure 4:
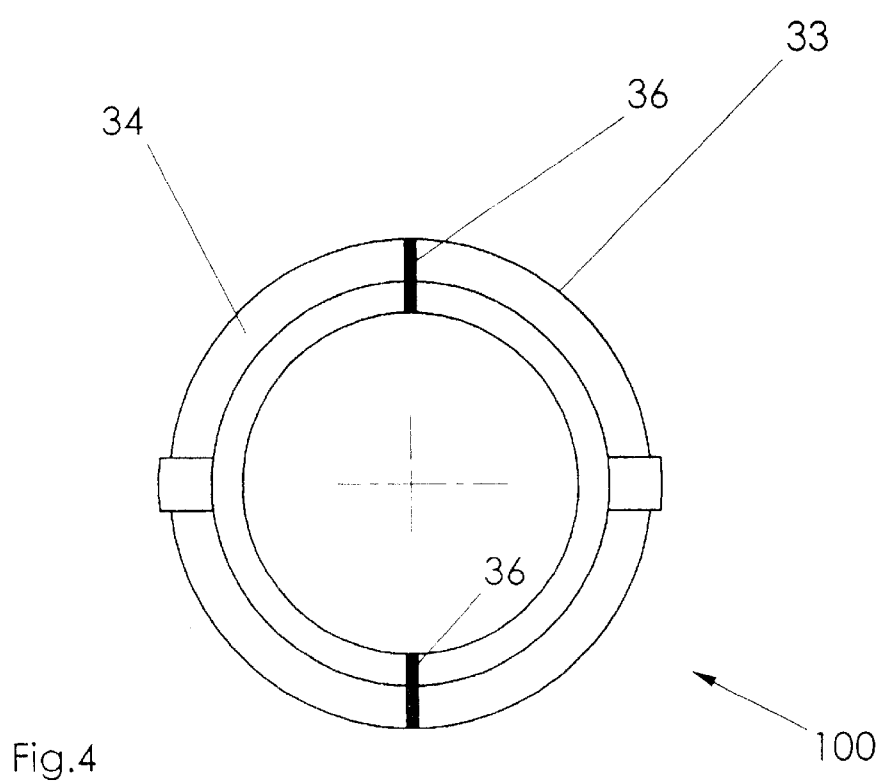
FIG. 4 is a top view of the cylinder adapter according to FIG. 3.

FIG. 4 shows a top view of the cylinder adapter 100 according to FIG. 3 with the sealing band 36, which connects the housing shells 33, 34.

While specific embodiments of the invention have been shown and described in detail to illustrate the application of the principles of the invention, it will be understood that the invention may be embodied otherwise without departing from such principles.

What is claimed is:

1. A device for releasing a gas to a respirator, the device comprising:
    a compressed gas cylinder containing gas and with a metering valve that can be opened by pressure, the metering valve having a tubular valve body letting through the gas and with a collar surrounding said valve body;
    a cylinder adapter with a locking mechanism for fastening on the collar, said adapter including a cylindrical wall part in the area of said valve body, said cylinder adapter having reduced strength properties defining a predetermined breaking point, said locking mechanism being destroyed by a breaking of said cylinder adapter along said breaking point during the removal of the cylinder adapter from said collar;
    a pressure body having a pressure part for actuating the valve body and having a gas channel for drawing off the gas to the respirator, said pressure body being connected to said wall part via a connection element for a stroke movement of said pressure body relative to said cylinder adapter and relative to said compressed gas cylinder.

2. A device in accordance with claim 1, wherein the connection element is a bayonet catch arrangement.

3. A device in accordance with claim 2, wherein the bayonet catch arrangement includes a groove limiting the stroke movement of the pressure body, said groove having a depression providing a locking position for a park position of the pressure body such that the valve body is positioned in the park position in a closed position.

4. A device in accordance with claim 1, wherein said locking mechanism comprises a support formed on the cylinder adapter adjacent to said collar and a support ring with a counterpiece arranged between a grip shell of the cylinder adapter and the compressed gas cylinder.

5. A device In accordance with claim 4, wherein the support is designed as a quadrant first groove and the counterpiece is designed as a quadrant-like second groove.

6. A device in accordance with claim 5, wherein the predetermined breaking point is designed as a notch extending in the connection area between the wall part and the grip shell and reduces the wall thickness.

7. A device in accordance with claim 4, wherein the predetermined breaking point is designed as a notch extending in the connection area between the wall part and the grip shell and reduces the wall thickness.

8. A device in accordance with claim 1, wherein the cylinder adapter comprises two housing shells arranged symmetrically to a vertical axis, the two housing shells being connected to one another at a partition line via a sealing band acting as a predetermined breaking point.

9. A device in accordance with claim 1, wherein the wall part has a gas type-specific coding.

10. A process for storing a gas for a respirator, the process comprising the steps of:
    providing a compressed gas cylinder as a storage medium for the gas with a metering valve having a valve body and having a collar surrounding the valve body;
    providing a cylinder adapter with a locking mechanism for fastening the cylinder adapter to the collar and with a cylindrical wall part in the area of said valve body;
    providing a pressure body having a pressure part for actuating the valve body and having a gas channel for drawing off the gas to the respirator;
    connecting said pressure body to the wall part via a connection element;
    connecting the cylinder adapter to the cylinder and fastening the cylinder adapter to the collar with the locking mechanism;
    forming the cylinder adapter with at least a region of reduced strength properties providing a predetermined breaking point with reduced strength properties on the cylinder adapter such that the ability to fasten the cylinder adapter to the cylinder with the locking mechanism is destroyed upon removing the cylinder adapter from the collar; and
    moving said pressure body relative to said cylinder adapter and relative to said compressed gas cylinder with the pressure body connected to said cylinder adapter via the connection element.

11. A process for storing a gas for a respirator, the process comprising the steps of:
    providing a compressed gas cylinder as a storage medium for the gas with a metering valve having a valve body sad having a collar surrounding the valve body;
    connecting a cylinder adapter to the cylinder and fastening the cylinder adapter to the collar with a locking mechanism including a support formed on the cylinder adapter adjacent to the collar and a support ring with a counterpiece; and
    forming the cylinder adapter with at least a region of reduced strength properties such that the ability to fasten the adapter to the cylinder is destroyed upon removing the adapter from the collar.

12. A process according to claim 11, further comprising:
    connecting a pressure body to the adapter with the pressure body having a pressure part for actuating the valve body and having a gas channel for drawing off the gas to the respirator; and
    providing a connection arrangement with interacting parts between the pressure body and a wall part of the cylinder adapter; and
    moving the pressure body via the connection arrangement in a stroke movement to draw off the gas to the respirator.

13. A process in accordance with claim 12, wherein the connection element is formed as a bayonet catch arrangement.

14. A process in accordance with claim 12, wherein the connection arrangement is formed as a bayonet catch arrangement including a groove limiting the stroke movement of the pressure body, said groove having a depression providing a locking position for a park position of the pressure body such that the valve body is positioned in the park position in the closed position.

15. A process in accordance with claim 12, wherein the wall part has a gas type-specific coding.

16. A process in accordance with claim 11, wherein the support ring with the counterpiece is arranged between a grip shell of the cylinder adapter and the compressed gas cylinder.

17. A process in accordance with claim 16, wherein the support is designed as a quadrant first groove and the counterpiece is designed as a quadrant second groove.

18. A process in accordance with claim 17, wherein the region of reduced strength properties is designed as a notch extending in the connection area between a wall part of the cylinder adapter and the grip shell and reduces the wall thickness.

19. A process in accordance with claim 16, wherein the region of reduced strength properties is designed as a notch extending in the connection area between a wall part of the cylinder adapter and the grip shell and reduces the wall thickness.

20. A process in accordance with claim 11, wherein the cylinder adapter comprises two housing shells arranged symmetrically to a vertical axis, the two housing shells being connected to one another at a partition line via a sealing band acting as a predetermined breaking point.

21. A device for releasing a gas to a respirator, the device comprising:

a compressed gas cylinder containing gas and with a metering valve that can be opened by the application of pressure to a portion of said metering valve, the metering valve having a tubular valve body letting through the gas and with a collar surrounding said valve body;

a cylinder adapter with a locking mechanism for fastening on the collar, said adapter including a cylindrical wall part in the area of said valve body and a support portion adjacent to said collar and including a support ring with a counterpiece adjacent to said collar, said counterpiece and said support portion cooperating to form said locking mechanism, said cylinder adapter having reduced strength properties defining a predetermined breaking point to allow said locking mechanism to be destroyed during the removal of the cylinder adapter from said collar;

a pressure body having a pressure part for actuating the valve body and having a gas channel for drawing off the gas to the respirator, said pressure body being connected to said wall part via a connection element for a stroke movement of said pressure body relative to said cylinder adapter and relative to said compressed gas cylinder.

22. A device for releasing a gas to a respirator, the device comprising:

a compressed gas cylinder containing gas and with a metering valve that can be opened by pressure, the metering valve having a tubular valve body letting through die gas and with a collar surrounding said valve body;

a cylinder adapter connected to said compressed gas cylinder by a locking means for fastening said cylinder adapter to said collar, said cylinder adapter including a cylindrical wall part in the area of said valve body, said cylinder adapter having reduced strength properties defining a predetermined breaking point to break along said breaking point upon disconnection of said cylinder adapter from said compressed gas cylinder, said locking means for no longer being capable of fastening said cylinder adapter to said collar upon the cylinder adapter breaking along said breaking point;

a pressure body having a pressure part for actuating the valve body and having a gas channel for drawing off the gas to the respirator, said pressure body being connected to said wall part via a connection element allowing a stroke movement of said pressure body relative to said relative to said cylinder adapter and relative to said compressed gas cylinder.

* * * * *